United States Patent [19]
Neigoff et al.

[11] Patent Number: 5,136,886
[45] Date of Patent: Aug. 11, 1992

[54] ACCELERATED WEATHERING AND LIGHTFASTNESS TESTING CHAMBER

[75] Inventors: Eugene N. Neigoff, Northbrook; Gene Comerford, Zion; James V. Huber, Oak Park; Victor H. Vlahos, Lake Zurich, all of Ill.

[73] Assignee: Atlas Electric Devices Co., Chicago, Ill.

[21] Appl. No.: 609,723

[22] Filed: Nov. 6, 1990

[51] Int. Cl.$^5$ ............................................. G01N 17/00
[52] U.S. Cl. ..................................... 73/865.6; 356/246
[58] Field of Search .......................... 73/856.6; 374/57; 356/246

[56] References Cited

U.S. PATENT DOCUMENTS

| | | | |
|---|---|---|---|
| 3,686,940 | 8/1972 | Kockott | 73/865.6 X |
| 3,713,727 | 1/1973 | Markosian et al. | 126/451 X |
| 3,797,918 | 3/1974 | Kockott | 73/865.6 X |
| 4,760,748 | 8/1988 | Katayanagi et al. | 73/865.6 |
| 4,817,447 | 4/1989 | Kashima et al. | 73/865.6 |
| 4,843,893 | 7/1989 | Huber et al. | 73/865.6 |
| 4,874,952 | 10/1989 | Arnaud et al. | 250/455.1 |
| 4,957,011 | 9/1990 | Huber et al. | 73/865.6 |

FOREIGN PATENT DOCUMENTS

| | | |
|---|---|---|
| 24840 | 2/1983 | Japan . |
| 2480037 | 10/1989 | Japan . |
| 2193329 | 2/1988 | United Kingdom . |

OTHER PUBLICATIONS

Brochure entitled SunSystem by Atlas Electric Devices Company of Chicago, Ill.; 4 pages; copyright 2-1988.

Primary Examiner—Tom Noland
Attorney, Agent, or Firm—Gerstman & Ellis, Ltd.

[57] ABSTRACT

A lightfastness testing chamber comprises an enclosure for samples being tested and at least one, and preferably a plurality of, lamps for irradiating samples in the enclosure. A monitor of the light intensity from each lamp present is provided. By this invention the monitor may comprise a light transmission rod, and preferably one such rod for each of the lamps, having one end positioned adjacent the lamp and another end in communication with light intensity measuring apparatus positioned more remotely from the lamp than the one end. The light transmission rod is preferably positioned on a side of the lamp that is substantially opposed to portions of the lamp that directly irradiate samples in the enclosure. Also, the samples may be moved by an elevatable platform or the like toward and away from the irradiating lamp or lamps to vary as desired the intensity of irradiation applied to the samples. Both curved and flat reflecting mirrors may be provided above the lamps to provide a desired uniformity of irradiation.

17 Claims, 5 Drawing Sheets

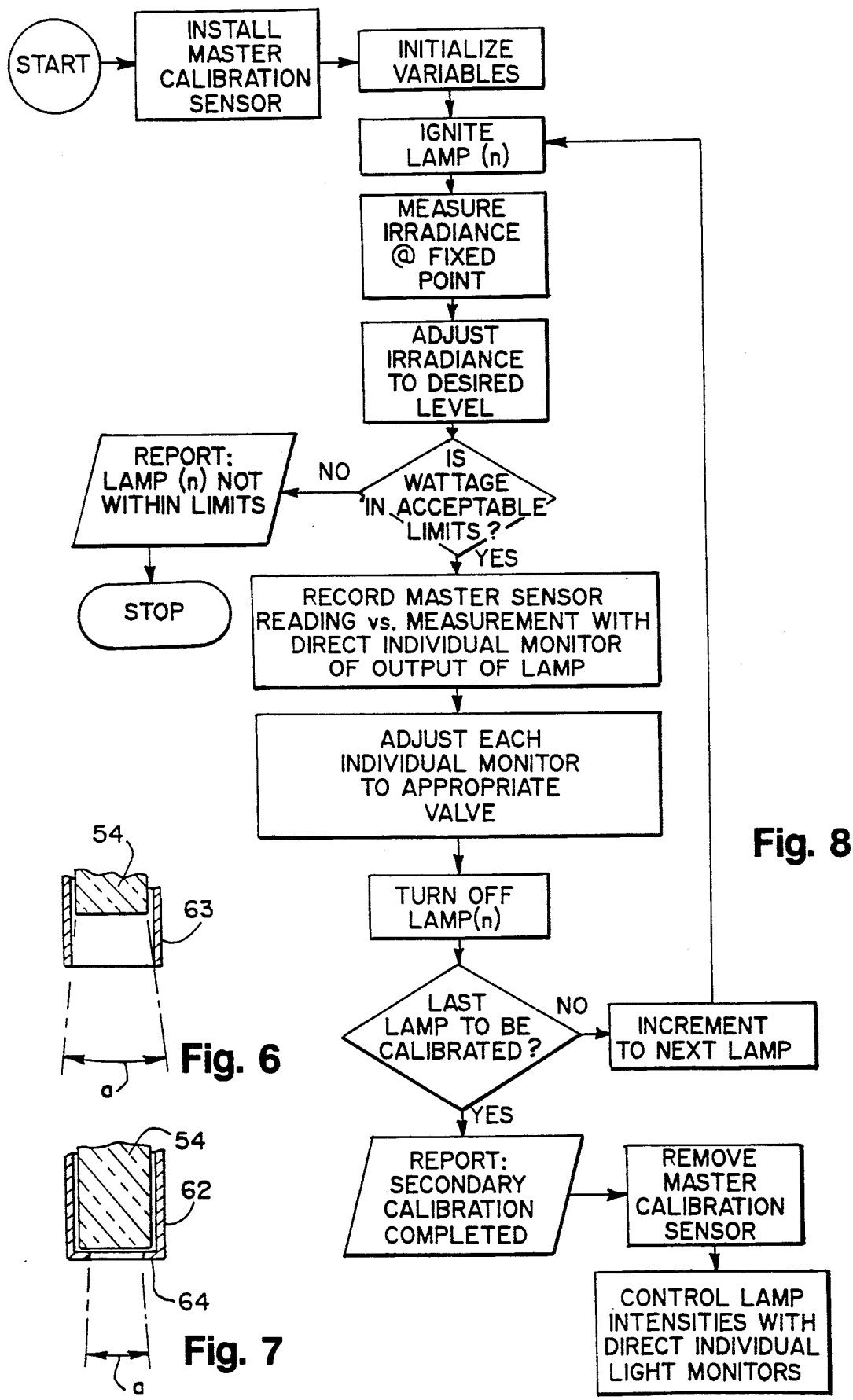

ACCELERATED WEATHERING AND LIGHTFASTNESS TESTING CHAMBER

BACKGROUND OF THE INVENTION

Chambers for the accelerated weathering and lightfastness testing of components such as fabrics, plastic items, painted surfaces and the like are generally known, for example being shown in Huber et al. U.S. Pat. No. 4,843,893 and Kashima et al. U.S. Pat. No. 4,817,447. Additionally, such testing machines can also test various items as to their resistance against heated air and humidity, or any or all of the above in combination, so that manufacturers can gain data as to the durability of their products on an accelerated basis, to simulate the effects of weathering, heat and the like.

In accordance with this invention, a component testing chamber is provided which is preferably built to large size, to allow the accelerated weathering and lightfastness testing of large components such as automotive dashboards or the like. Since the component testing chamber of this invention is large, preferably a plurality of light emission lamps are used, which light emission lamps may be xenon type lamps, metal halide lamps, fluorescent lamps, ultraviolet lamps, infrared lamps and the like. The term "light" is intended to include frequencies beyond the visible spectrum.

Since the radiation stability testing performed in the testing chamber of this invention needs to be quantitative and reproducible, there is a need for conveniently determining that the intensity of the radiation received by components or samples being tested is that which is expected. By this invention, simple and effective means are provided for the constant irradiance, on a continuing basis, in the testing chamber even though the light emission from various lamps may vary as the lamps age through continued use. Simple means are provided for automatically adjusting the radiation intensity provided to the samples being tested within the chamber of this invention, with the chamber of this invention preferably providing improved uniformity of irradiation in the various positions that samples may occupy within the chamber.

DESCRIPTION OF THE INVENTION

In this invention, an accelerated weathering and lightfastness testing chamber is provided which comprises an enclosure for samples being tested. At least one lamp is provided for irradiating samples in the enclosure. Means are provided for monitoring the light intensity from the lamp.

In accordance with this invention, the monitoring means comprises light transmission means having one end positioned adjacent the lamp and another end in communication with light intensity measuring means, which are positioned more remotely from the lamp than the one end of the rod is positioned. The light transmission means is positioned on a side of the lamp that is substantially opposed to portions of the lamp that directly irradiate samples in the enclosure. Thus, the light transmission means does not interfere with the propagation of radiation from the lamp to the samples. The light transmission means may be a transparent rod, fiber optic cable, or even an open tube, for example.

A plurality of the lamps as described above may be provided. In this circumstance, separate light transmission means such as rods may also be provided, each respectively having its one end as defined above positioned adjacent a separate lamp. Each of the rods communicates with the light intensity measuring means, typically through its other end. Control means are provided for independently controlling the light intensity emitted from each lamp.

Thus, the individual light output of each separate lamp may be separately monitored and controlled, to provide the desired light intensity to the samples being irradiated.

The light transmission means such as rods or cables may, if desired, be equipped with means for limiting light transmission through the rod or cable to substantially limit that light which is emitted by the particular lamp to which the light transmission rod or cable relates. This limiting means may comprise an opaque sleeve carried in coaxial manner about the one end of the light transmission rod or cable defined above, to limit the light acceptance angle of the rod at its one end. Alternatively, the limiting means may comprise an opaque, annular stop member carried at the one end of a light transmission rod.

Also, the enclosure may carry means for retaining in predetermined positions the samples being tested. Means may also be provided for moving the samples being tested toward and away from the irradiating lamp or lamps, to vary as desired the intensity of irradiation applied to the samples. This may be accomplished by placing the samples to be tested on a platform, with means for elevating and lowering the platform toward and away from the lamp or lamps being provided.

Additionally, the testing chamber of this invention may be equipped with reflecting mirrors which are provided above the lamp, to direct light from the lamp toward the samples. Some of the reflecting mirrors are concave, to at least partially focus reflected light toward said samples. Other of the reflecting mirrors are substantially flat, to direct broad areas of reflected light toward said samples. By this means, an increase in the uniformity of irradiation throughout the testing chamber can be provided, so that the various samples receive substantially equal amounts of irradiation in equal times of exposure, irrespective of the positions at which they are retained within the testing chamber.

Specifically, at least a pair of lamps may be positioned in side-by-side relation in the testing chamber. The reflecting mirrors may comprise a plurality of flat mirrors forming a pair of sections extending in cross-section laterally from a region essentially between the lamps, above and outwardly of said lamps, with each lamp occupying an approximate focus of one of said sections, plus a curved, generally cylindrically sectioned mirror positioned laterally outwardly from said flat mirrors.

Additionally, a method is provided by this invention of calibrating the light output of a multi-lamp lightfastness testing chamber, in which the chamber interior dimension defines a sample testing area. The method comprises: sequentially turning on and then off each lamp by itself, while measuring from said sample testing area the irradiation provided by each lamp and adjusting in response thereto the intensity of irradiation from each lamp to a desired level, and also sensing with individual light monitor means the light intensity of each individual lamp from a side of each lamp that is substantially opposed to portions of each lamp that directly irradiate said sample testing area, whereby the light intensity of said lamps may each be subsequently sensed with said individual monitor means, and the intensity of said irradiation provided at the sample area may be simultaneously controlled by maintaining the sensed light intensity of each lamp within predetermined limits.

Accordingly, by this invention a lightfastness testing chamber may be provided which exhibits the advantages described above, and generally exhibits great flexibility of use, being capable of testing large, manufactured items, while the light output of individual lamps may be continuously monitored and controlled, and may be correlated to an absolute standard as well, and in which great uniformity of irradiation, compared with prior art systems, and great ease of the adjustment of the radiation intensity may be provided.

DESCRIPTION OF THE DRAWINGS

In the drawings.

FIGS. 6 and 7 are each enlarged, fragmentary, detailed sectional views of different embodiments of a portion of FIG. 4; and FIG. 8 is a flow chart illustrating how the individual lamp irradiance may be calibrated, to indirectly control and quantify the irradiance received by the samples for irradiation within the testing chamber.

DESCRIPTION OF SPECIFIC EMBODIMENTS

Figure 1:
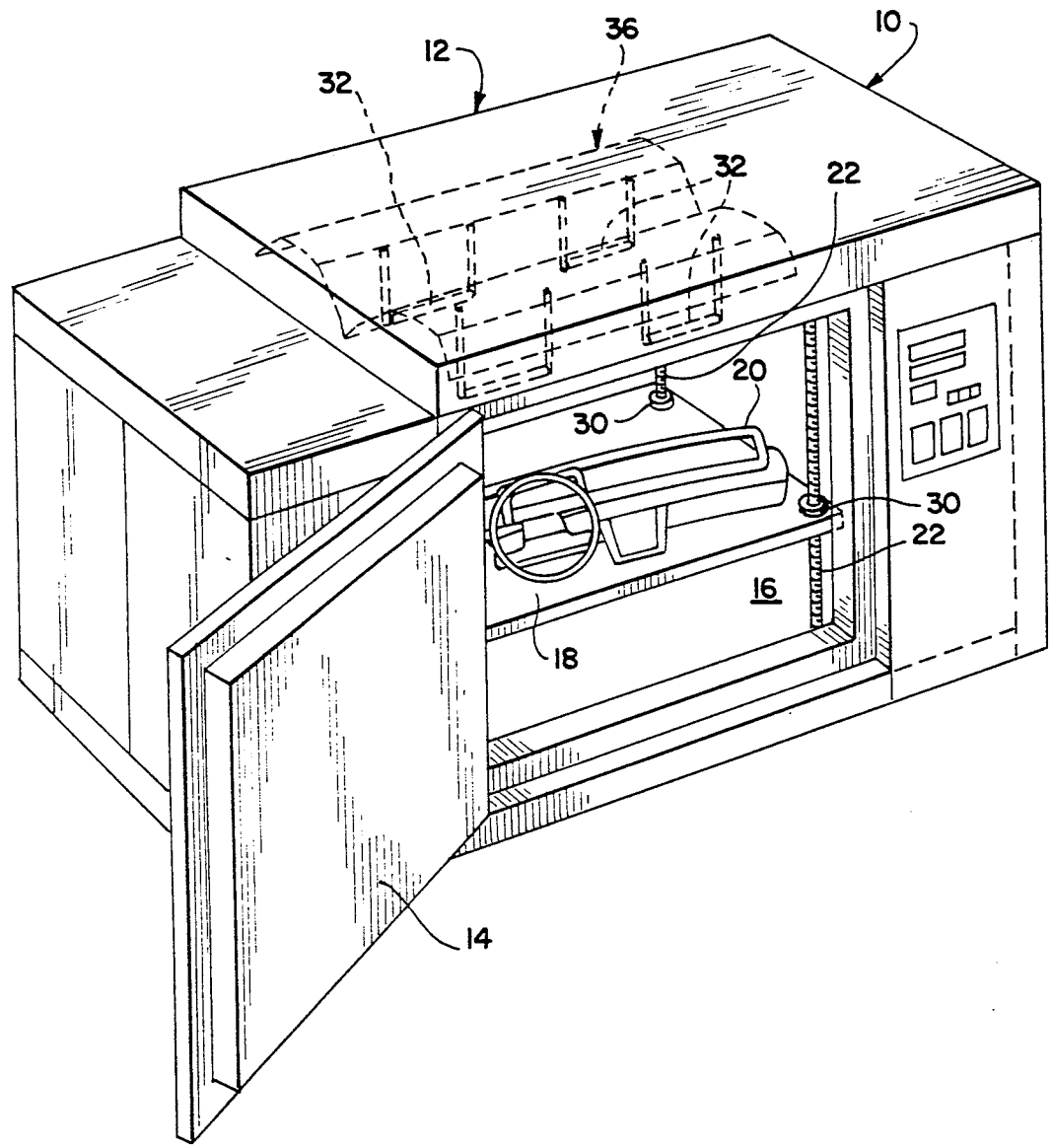
FIG. 1 is a perspective view of a lightfastness testing chamber of this invention.

Referring to the drawings, FIG. 1 shows a lightfastness testing chamber 10 which comprises an enclosure 12 having a front door 14 and an inner chamber 16, which carries a platform 18 for holding samples 20 to be tested. In the specific instance shown in FIG. 1, the sample to be tested is the dashboard of an automobile.

Figure 2:
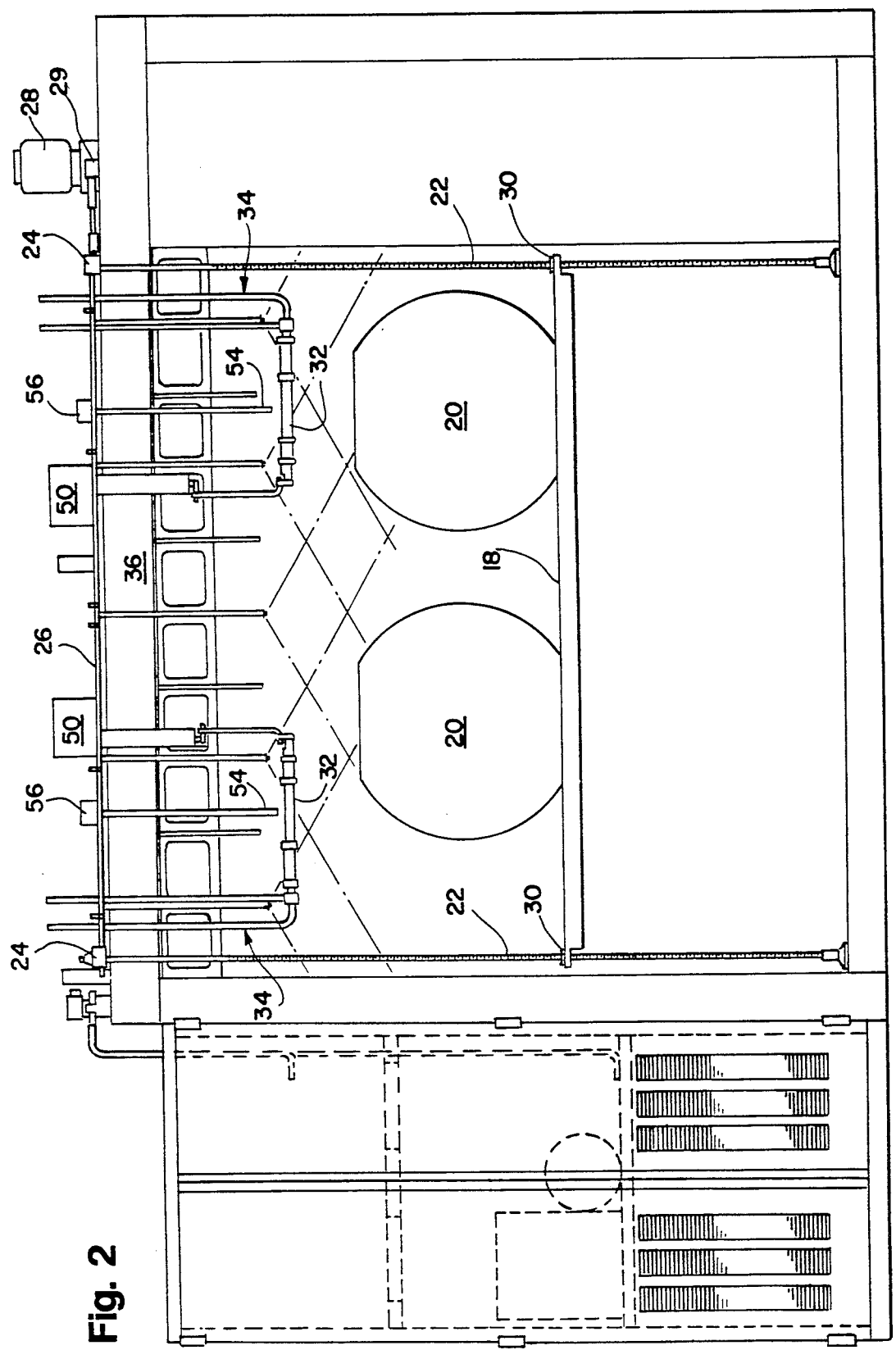
FIG. 2 is a front elevational view, with front portions broken away, of the lightfastness testing chamber of FIG. 1.
Figure 3:
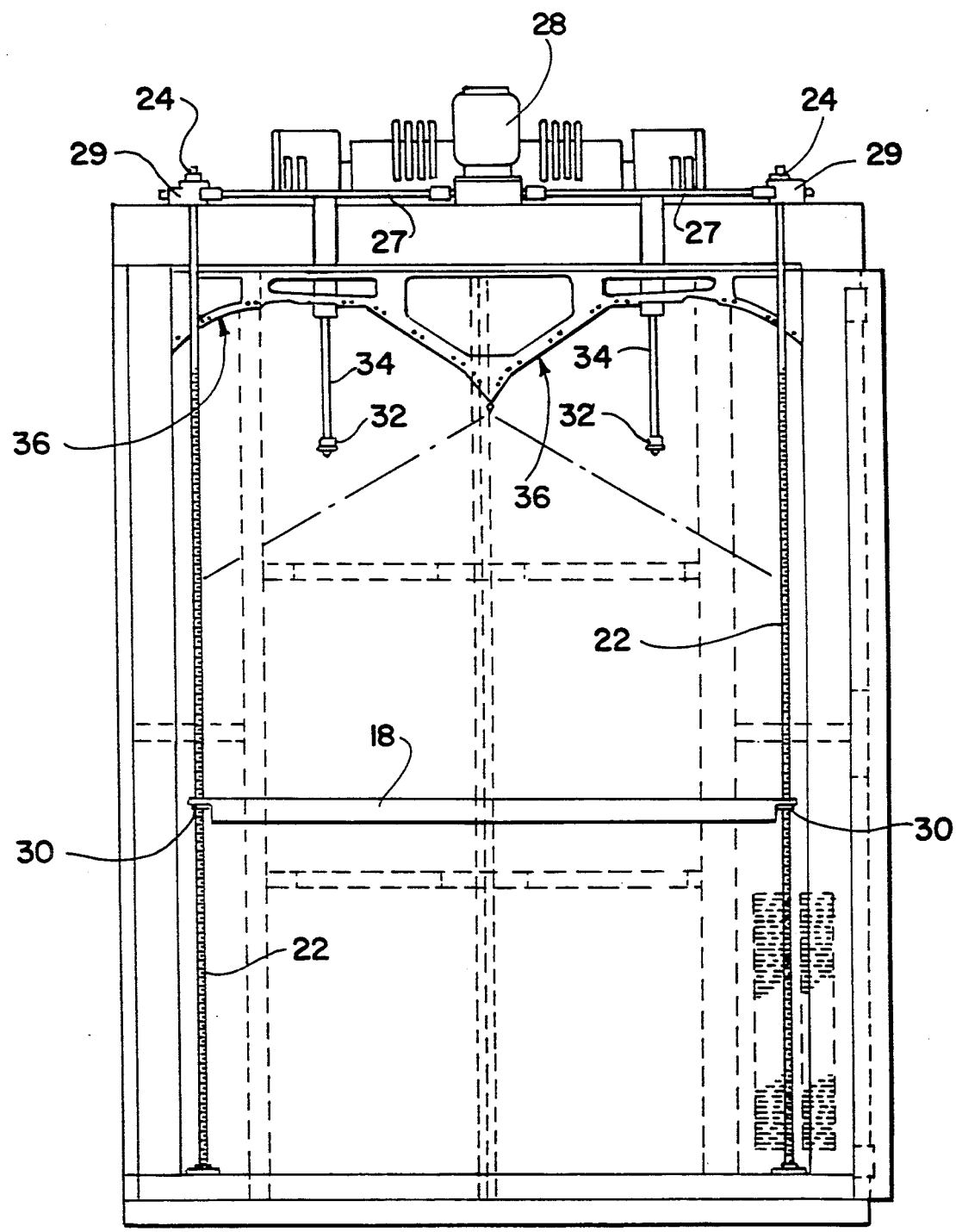
FIG. 3 is a side elevational view, with portions broken away, of the lightfastness testing chamber of FIG. 1.

Platform 18 is carried at each of its four corners by threaded support rods 22 which are each rotatable by a rotating shaft powered unit 24. As shown particularly in FIGS. 2 and 3, power units 24 that rotate shafts 22 are connected by transverse shafts 26, 27 to a reversible gear motor 28. All four of the respective threaded shafts 22 are connected via rotating shaft powered units 24 and transverse shafts 26, 27 to this motor so that vertical threaded shafts 22 are rotated together in a uniform manner in either direction. Then, a fixed nut 30 is carried at each corner of platform 18 so that, as threaded shafts 22 uniformly rotate, platform 18 rises or falls. Alternatively, this movable stage could also use scissor jacks or other means of elevation. Thus, the samples to be tested 20 can be brought nearer to or farther from lamps 32 with platform 18, which lamps are positioned at the top of chamber 16 to provide irradiation to samples 20. Specifically, lamps 32 may be xenon lamps, metal halide lamps, fluorescent lamps, or, if desired, ultraviolet or infrared emitting lamps, or combinations thereof.

Angled turns may be provided in transverse rotating shafts 26, 27 by conventional 90 degree miter gear boxes 29, where they may be needed.

As one significant advantage of the above arrangement, it becomes possible to vary the intensity of radiation applied to any of samples 20 during operation of the apparatus, without shutting off power to lamps 32. This is simply accomplished by raising or lowering platform 18 by means of motor 28, during a light-irradiation procedure if desired. Accordingly, the intensity of the light irradiation on the samples can be monitored, and can be made to conform to a predetermined standard by the simple operation of motor 28.

Lamps 32 are carried in brackets 34 as shown, with a reflecting mirror arrangement 36 being provided. As shown particularly in FIG. 1, reflecting mirror arrangement 36 defines a pair of trough-like structures which generally extend in the direction of extension of each of lamps 32.

Figure 5:
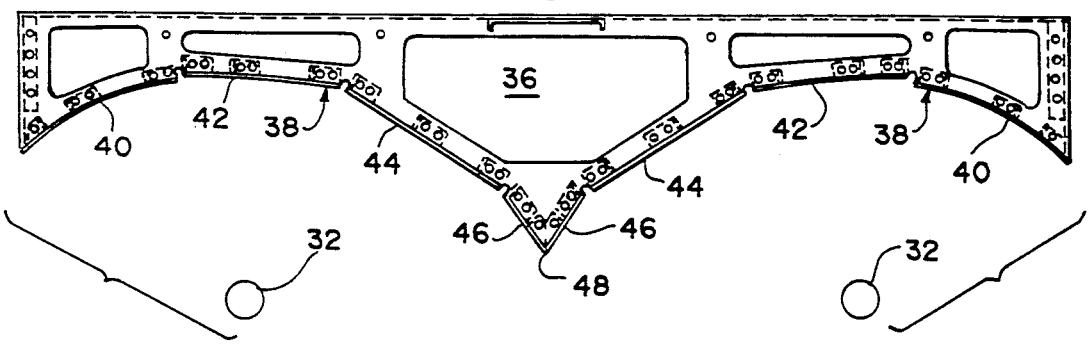
FIG. 5 is an enlarged, fragmentary, detailed, transverse sectional view of two of the lamps in side-by-side relation and the mirror arrangement above said lamps of the testing chamber of FIG. 1.

Referring specifically to FIG. 5, a pair of lamps 32 is shown, with the mirror arrangement 36 and each of their trough like structures 38 also shown. Specifically, in mirror arrangement 36, some of the mirrors 40, 42 are concave to at least partially focus reflected light toward the samples. Other of the reflecting mirrors 44, 46 are substantially flat, to direct broad areas of reflected light toward the samples.

As specifically shown, the pair of lamps 32 shown in FIG. 5 are positioned in side-by-side relation, and flat mirrors 44, 46 form a pair of sections which extend (in cross section) laterally (as shown in FIG. 5) from a region 48 which is essentially between lamps 32, with the flat sections extending in cross section above in an outward direction relative to said lamps. Also, each of lamps 32 is at the approximate focus of one of those sections defined respectively by a pair of flat mirrors 44, 46. Additionally, mirror 42, while virtually flat, does preferably have a small amount of curvature. Mirror 40, as shown, has a perceptible amount of curvature to focus light as desired. These curved mirrors, as shown, are positioned laterally outwardly from the flat mirrors.

By such an arrangement, it becomes possible to provide an improved degree of uniformity of irradiation to the surface of platform 18 where the samples to be tested reside. Such an arrangement can minimize the differences of radiation received at differing areas of the platform.

Figure 4:
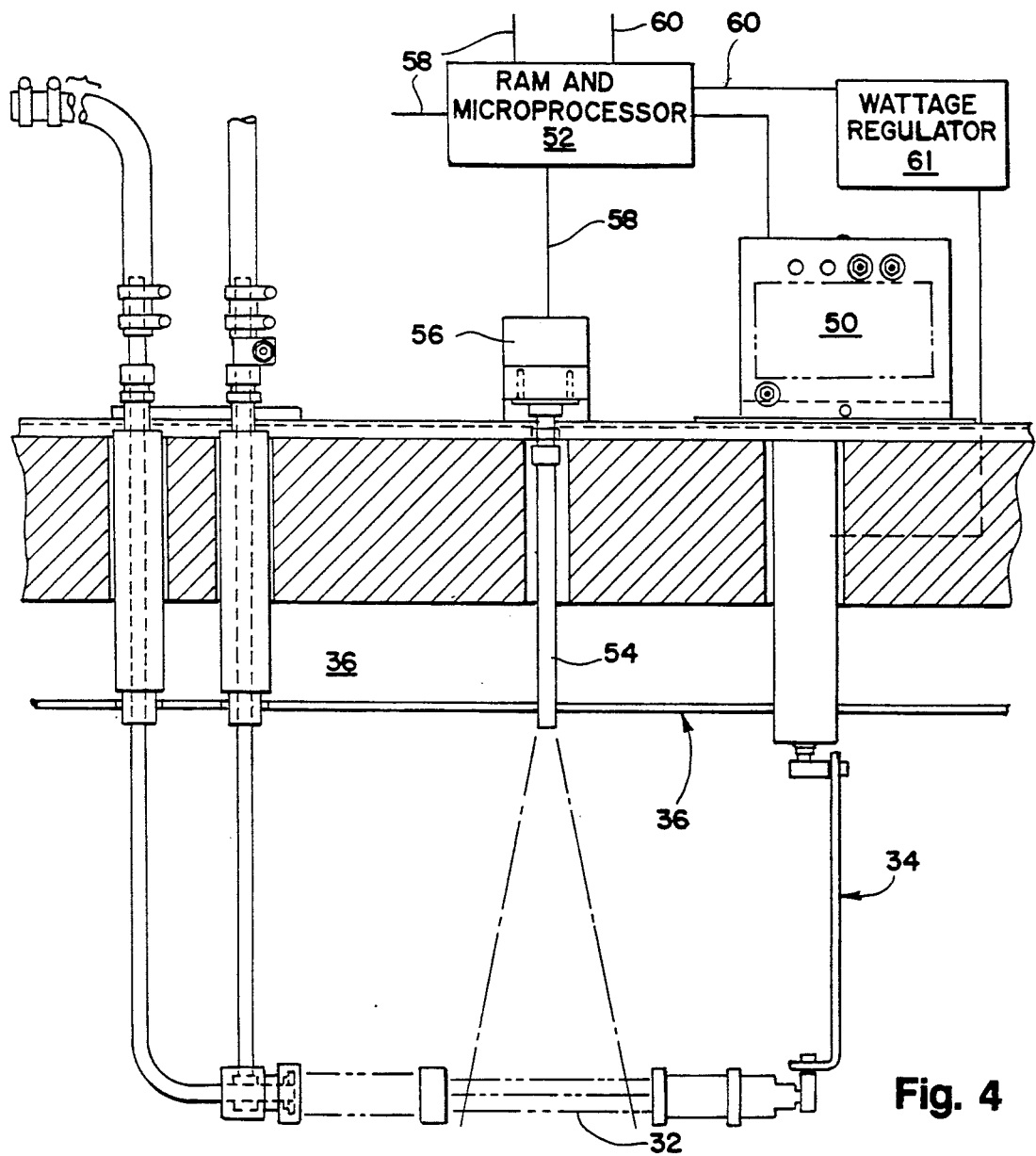
FIG. 4 is an enlarged, elevational view, taken partly in section, of a single lamp of the testing chamber of FIG. 1 and its related components.

FIG. 4 illustrates an enlarged view of an individual lamp 32, its bracket 34, and related parts. An individual lamp igniter 50 is provided for each lamp. The intensity of output of lamp 32 is controlled by RAM and microprocessor 52 through an individual wattage regulator 61. Lamps 32, their brackets 34, and their electric circuitry may be conventional except as otherwise described herein. Alternatively, RAM and microprocessor 52 may be replaced by analog circuitry.

By this invention, a light transmission rod 54 is positioned to pass through the upper mirror arrangement 36 and to point directly at lamp 32, from a side of the lamp which is substantially opposed to portions of lamp 32 that directly irradiate samples 20 in the enclosure. See for example FIG. 2 for the positioning of light transmission rods 54 with respect to the respective lamps 32 and platform 18, where the respective samples are carried. Thus, each light rod 54 conveys light transmitted by its own lamp 32 to a light intensity sensor 56, which may be of a conventional design. The light intensity sensed by sensor 56 is then converted to an electronic signal which passes to microprocessor 52 through a wire 58.

The situation shown in FIG. 4 is duplicated for each of lamps 32, so that signals responsive to the light intensity sensed from each of lamps 32 is provided to microprocessor 52 as a separate electronic input through the respective wires 58.

Similarly, microprocessor 52, as stated before, defines electronic outputs 60 to wattage regulators 61, which separately communicate with the individual lamps 32, so that microprocessor 52 can adjust the intensity of emission of each lamp 32 on an individual basis in a manner which is responsive to the feedback received through sensor 56 in each instance.

Thus, by this invention, the output of the respective lamps 32 can be continuously monitored and adjusted to fit a predetermined, desired standard by three means:
1. Simply by raising or lowering platform 18 by means of motor 28;
2. By the controller (Analog or RAM and Microprocessor) 52, changing the output of lamps 32 through the wattage regulator 61, using inputted data; or
3. A combination of the above two methods.

Accordingly, the intensity of the light (irradiance) on the sample can be controlled, and continuous adjustment can be made to conform with the testing requirements required by the appropriate test procedure.

Also because of this, it can be assured that the actual irradiation provided to the respective samples 20 on different runs of the lightfastness testing chamber can be readily correlated with each other for accurate lightfastness and other stability data.

As shown in FIG. 6, the lower tip of light transmission rod 54 may be sheathed with a metal sleeve 63, which may extend the entire length of rod 54 if desired. Sleeve 63 may extend below the lower end of light transmission rod 54, to limit the angle a of light acceptance to rod 54 and thus to sensor 56. This expedient can help in assuring that the only significant light that passes through each light rod 54 to its respective sensor 56 is light directly emitted from the associated lamp 32. Thus, the independence of the data received from each sensor 56 is assured in that the light emission from each separate lamp 32 is separately sensed with less interference from other light sources, particularly the other lamps.

Referring to FIG. 7, as an alternative, light rod 54 may carry a similar sleeve 62, in which the lower end of the sleeve 62 defines an inner flange 64 to limit the aperture at the lower end of the light rod. This also can serve to make the light rod more selective as to the source of light that it receives, so that only the light from the associated lamp 32 is sensed by a given sensor 56.

FIG. 8 illustrates a method for calibrating the irradiance of the individual lamps to a quantitative level. Once this is done, the relative data provided by the sensors 56 and microprocessor 52 in accordance with this invention is correlated with absolute data, to provide a desired, quantitative irradiance from each of lamps 32 to samples on platform 18.

As a first step, one places a master calibrator sensor on platform 18. Such known sensors are able to provide quantitative sensing of the radiation from lamps 32, to provide a numerical readout of the intensity thereof.

After initializing of all variables, a first of the lamps 32 is ignited. The irradiance is measured by the master calibration sensor, and the intensity of radiation of the lamp 32 is adjusted to the desired level as indicated by the numerical readout of the master calibration sensor.

The lamp wattage is then monitored and if not within desired limits the lamp should be removed and replaced. Otherwise, the process continues.

One then records the master sensor output verses the measurement of individual lamp irradiation output, as measured with the associated individual monitoring apparatus, namely light rod 54 and light sensor 56.

Then, each individual light monitoring system comprising the light monitor 56 and the individual wattage regulator 61, controlled through ROM and microprocessor 52, can be adjusted to maintain the appropriate value sensed by the individual light monitor as a correlation with the master sensor output.

The same process is then performed with respect to the next lamp, with the irradiance data being stored with respect to each lamp until all lamps have been thus calibrated. Following this, one removes the master calibration sensor.

From that time on, it can be known that the given irradiation output sensed for each lamp will result in a known total irradiance at the sample site. This calibration data remains good until the operating characteristics of the system change with aging. The above has been offered for illustrative purposes only, and is not intended to limit the scope of the invention of this application, which is as defined in the claims below.

That which is claimed is:

1. In a lightfastness testing chamber which comprises an enclosure for samples being tested, at least one lamp for irradiating samples in said enclosure, and means for monitoring the light intensity from the lamp, the improvement comprising, in combination: said monitoring means comprising a light transmission rod having one end positioned adjacent said lamp and another end in communication with light intensity measuring means positioned more remotely from the lamp than the one end, said light transmission rod being positioned on a side of said lamp that is substantially opposed to portions of said lamp that directly irradiate samples in said enclosure.

2. The testing chamber of claim 1 which comprises a plurality of lamps, and separate light transmission rods, each respectively having one end positioned adjacent a separate lamp, each rod communicating with light intensity measuring means, and control means for independently controlling the light intensity from each lamp in a manner responsive to the light intensity measuring means.

3. The testing chamber of claim 1 in which said light transmission rod is equipped with means for limiting light transmission through said rod to substantially that light which is emitted by said lamp.

4. The testing chamber of claim 3 in which the limiting means comprises an opaque sleeve carried in coaxial manner about the one end of said light transmission rod, to limit the light acceptance angle of said rod at its one end.

5. The testing chamber of claim 3 in which the limiting means comprises an opaque annular stop member carried at the one end of said light transmission rod.

6. The testing chamber of claim 1 in which said enclosure carries means for retaining in predetermined positions said samples being tested, plus means for moving said samples being tested toward and away from said irradiating lamp, to vary as desired the intensity of irradiation applied to said samples.

7. The testing chamber of claim 1 in which reflecting mirrors are provided above said lamp to direct light from said lamp toward said samples, some of said reflecting mirrors being concave to at least partially focus reflected light toward said samples, and other of said reflecting mirrors being substantially flat to direct broad areas of reflected light toward said samples.

8. The testing chamber of claim 7 in which at least a pair of lamps are positioned in side-by-side relation, said reflecting mirrors comprising a plurality of flat mirrors forming a pair of sections extending in cross-section laterally from a region essentially between said lamps in a direction extending above and outwardly of said lamps, with each lamp occupying an approximate focus of one of said sections, and at least one curved, generally cylindrically sectioned mirror positioned laterally outwardly from said flat mirrors.

9. In a lightfastness testing chamber which comprises an enclosure for samples being tested, a plurality of lamps for irradiating samples in said enclosure, and means for monitoring the light intensity from said lamps, the improvement comprising, in combination: a plurality of separate light transmission rods, each respectively having one end positioned adjacent to a separate lamp of said plurality of lamps, each of said light transmission rods being in communication with light intensity measuring means positioned more remotely from its associated lamp than the one end of said light transmission rod, each light transmission rod being positioned on a side of its associated lamp that is substantially opposed to portions of that lamp that directly irradiate samples in said enclosure, said light transmission rods being each equipped with means for limiting light transmission therethrough to substantially that light which is emitted by the lamp with which each light transmission rod is associated; and control means for independently controlling the light intensity from each lamp.

10. The testing chamber of claim 9 in which said enclosure carries means for retaining in predetermined positions said samples being tested, plus means for moving said samples being tested toward and away from said irradiating lamps, to vary as desired the intensity of irradiation applied to said samples.

11. The testing chamber of claim 10 in which reflecting mirrors are provided above said lamps to direct light from said lamps toward said samples, some of said reflecting mirrors being concave to at least partially focus reflected light toward said samples, and other of said reflecting mirrors being substantially flat to direct broad areas of reflected light toward said samples.

12. The testing chamber of claim 11 in which at least a pair of said lamps are positioned in side-by-side relation, said reflecting mirrors comprising a plurality of flat mirrors forming a pair of sections extending in cross-section laterally from a region essentially between said lamps in a direction extending above and outwardly of said lamps, with each lamp occupying an approximate focus of one of said sections, and at least one curved, generally cylindrically sectioned mirror positioned laterally outwardly from said flat mirrors.

13. A lightfastness testing chamber which comprises an enclosure for samples being tested, a plurality of lamps for irradiating samples in said enclosure, and means for monitoring the light intensity from said lamps, said means comprising separate light transmission rods, each respectively having one end thereof positioned adjacent a separate lamp, each said rod communicating with light intensity measuring means at its other end, and control means for independently controlling the light intensity from each lamp in a manner responsive to the light intensity measuring means.

14. The testing chamber of claim 13 in which said light transmission are equipped with means for limiting light transmission therethrough to substantially that light which is emitted by the lamp with which said rod is associated.

15. In a lightfastness testing chamber which comprises an enclosure for samples being tested, at least one lamp for irradiating samples in said enclosure, the improvement comprising, in combination: said enclosure carrying means for retaining in predetermined positions said samples being tested, plus means for moving said samples being tested toward and away from the irradiating lamp to vary as desired the intensity of irradiation applied to said samples, said means for retaining in predetermined positions the samples being tested and said moving means comprising a raisable and lowerable platform, whereby said samples may be moved to varying distances from said lamp without shutting off power to said lamp; and reflecting mirrors provided above said lamp, to direct light from said lamp toward said samples, some of said reflecting mirrors being concave to at least partially focus reflected light toward said samples, and other of said reflecting mirrors being substantially flat to direct broad areas of reflected light toward same samples.

16. In a lightfastness testing chamber which comprises an enclosure for samples being tested, at least a pair of lamps for irradiating samples in said enclosure, reflecting mirrors positioned to direct light from said lamps toward said samples, some of said reflecting mirrors comprising a plurality of flat mirrors forming a pair of sections extending in cross-section laterally from a region essentially between said lamps in a direction above and outwardly of said lamps, with each lamp occupying an approximate focus of one of said sections, and curved, generally cylindrically sectioned mirrors positioned laterally outwardly from said flat mirrors.

17. The testing chamber of claim 16 which includes separate light transmission rods, each respectively having one end positioned adjacent a separate lamp, each said rod communicating through its other end with light intensity measuring means, and control means for independently controlling the light intensity from each lamp in a manner responsive to the light intensity means.

* * * * *